(12) United States Patent
Bukhary

(10) Patent No.: US 9,066,775 B2
(45) Date of Patent: Jun. 30, 2015

(54) ORTHODONTIC SYSTEM

(75) Inventor: Mohammed Taher Bukhary, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 13/370,538

(22) Filed: Feb. 10, 2012

(65) Prior Publication Data
US 2013/0040260 A1    Feb. 14, 2013

(30) Foreign Application Priority Data
Feb. 15, 2011 (EP) ..................... 11001228

(51) Int. Cl.
A61C 3/00 (2006.01)
A61C 7/20 (2006.01)
A61C 7/22 (2006.01)

(52) U.S. Cl.
CPC .... A61C 7/20 (2013.01); A61C 7/22 (2013.01)

(58) Field of Classification Search
CPC .............. A61C 7/20; A61C 7/22; A61C 7/26; A61C 7/28
USPC .......................... 433/8, 10, 15, 18, 20, 22, 24
See application file for complete search history.

(56) References Cited

U.S. PATENT DOCUMENTS

| | | | |
|---|---|---|---|
| 1,638,006 A * | 8/1927 | Aderer | 602/5 |
| 2,259,160 A * | 10/1941 | Glaser | 433/19 |
| 2,494,540 A * | 1/1950 | Brusse | 433/15 |
| 2,495,692 A * | 1/1950 | Brusse | 433/8 |
| 3,028,671 A * | 4/1962 | Berger | 433/8 |
| 3,055,111 A * | 9/1962 | Kesling | 433/10 |
| 3,061,929 A * | 11/1962 | Jarabak | 433/15 |
| 3,262,207 A * | 7/1966 | Kesling | 433/10 |
| 3,374,542 A * | 3/1968 | Moylan, Jr. | 433/8 |
| 3,593,421 A * | 7/1971 | Brader | 433/21 |
| 3,775,850 A * | 12/1973 | Northcutt | 433/16 |
| 4,197,643 A * | 4/1980 | Burstone et al. | 433/20 |
| 4,268,250 A * | 5/1981 | Reeve | 433/20 |
| 4,424,033 A * | 1/1984 | Wool | 433/20 |
| 5,092,768 A * | 3/1992 | Korn | 433/18 |
| 5,131,843 A * | 7/1992 | Hilgers et al. | 433/20 |
| 5,474,444 A * | 12/1995 | Wildman | 433/8 |
| 5,580,243 A * | 12/1996 | Bloore | 433/6 |
| 5,823,772 A * | 10/1998 | Vogt | 433/21 |
| 6,595,774 B1* | 7/2003 | Risse | 433/21 |
| 7,887,324 B2* | 2/2011 | Singh | 433/7 |
| 2005/0244781 A1* | 11/2005 | Abels et al. | 433/24 |
| 2009/0087810 A1* | 4/2009 | Singh | 433/24 |
| 2010/0015565 A1* | 1/2010 | Carrillo Gonzalez et al. | 433/7 |

* cited by examiner

*Primary Examiner* — Cris L Rodriguez
*Assistant Examiner* — Mirayda A Aponte
(74) *Attorney, Agent, or Firm* — Renner, Otto, Boisselle & Sklar, LLP

(57) ABSTRACT

The invention relates to an orthodontic system which comprises a main wire having first and second end sections and at least one looped section there between, and a support wire, the main wire further having at least one coupling means for coupling to the support wire, the coupling means being arranged on the at least one looped section, and fastening means for fastening the main wire and the support wire to a patient's teeth.

11 Claims, 5 Drawing Sheets

ORTHODONTIC SYSTEM

The present application claims benefit of and priority under 35 U.S.C. §119 to European Application No. 11001228.3, filed 15 Feb. 2011, the entirety of which is hereby incorporated herein by reference.

The present invention relates to an orthodontic system and, in particular to an orthodontic system for treating malocclusion including retrusion of a patient's teeth. In more detail, the present invention relates to an orthodontic system for applying protraction forces to the upper or lower anterior teeth of a patient.

In the document GB 974,100 an orthodontic device is disclosed comprising a torque-applying wire element. The wire element includes vertical bent extensions which are kept in place by means of edgewise brackets with slots to receive the wire.

The known device is difficult to apply to a patient's teeth and is, moreover, likely to cause injuries due to the free standing wire extensions. It is therefore desirable to provide an orthodontic system which is easy to apply, robust, comfortable to wear and which minimizes pain and injuries when being applied to a patient.

The problem is solved by an orthodontic system according to claim 1.

In particular, the present invention provides an orthodontic system comprising: a main wire having first and second end sections and at least one looped section there between and a support wire, the main wire further having at least one coupling means for coupling to the support wire, the coupling means being arranged on the at least one looped section, and fastening means to fasten the main wire and the support wire to the patient's teeth.

With the orthodontic system of the present invention, a protraction force may be applied to a patient's teeth using the main wire. By applying the main wire to the patient's denture, a tension force is created along the main wire, which may be directed by means of the looped section. Here, the looped section creates a tension force along the main wire. Moreover, when being applied to a patient's teeth, the main wire is bend following a curvature of the patient's teeth generating a constrained state of the main wire. In this constrained state, the angular orientation of the looped section affects the direction of the forces acting on the main wire. As will be described in more detail below, the looped section is directed in a substantially anterior, i.e. labial direction when the main wire is applied. Rotating the looped sections to a substantially caudal direction, when the system is applied to the lower anterior teeth, or to a substantially cranial direction, when the system is applied to the upper anterior teeth, will cause a generally anteriorly directed force on the main wire. By attaching the main wire to the anterior teeth, eg. by brackets normally used to fix orthodontic appliances to a patient's teeth, the labially directed force is transferred to the teeth, giving rise to a protraction force on the teeth.

The support wire according to the present invention is coupled to the looped section when applying the system to a patient's teeth. By coupling the support wire to the looped section, the looped section may be rotated, thereby adjusting the orientation of the forces described above. Moreover, the support wire facilitates fixing the position of the looped section when rotated to its final position.

The at least one looped section may, in particular, comprise a u-, v-, w-, or m-shaped section, a half-circle, a coil or that like. Moreover, the looped section may in some embodiments comprise two leg sections, preferably parallel to each other, defining a clearance along a principal line of extension of the main wire.

The coupling means is, moreover, arranged on the at least one looped section. Hence, the coupling means is arranged remote from a principal line of extension of the main wire.

In particular, the coupling means may be arranged at an apex of the at least one looped section. This results in a large leverage effect then fixing the rotation of the looped section. Moreover, the coupling means may further generate an additional tension on the main wire.

In a preferred embodiment, the main wire further has at least two, in particular at least three and preferably five looped sections arranged in series between the first and second end sections. Increasing the number of looped sections along the main wire allows a tailored adjustment of the main wire. In particular, the number of looped sections of the main wire may be chosen in accordance with the number of teeth to be treated. For example, the looped sections may be arranged such that in the applied state, the looped sections lie in front of the transitions between adjacent teeth. Here, providing three looped sections is especially advantageous for treating the four anterior teeth comprising three transitions. Providing five looped sections is, moreover, advantageous for treating the four anterior teeth and the two canines. The looped sections may, in particular, be oriented in the substantially same direction along the main wire if the main wire is in an unconstrained state.

According to an even more preferred embodiment, each two adjacent looped section are interconnected by a respected base section. This provides the possibility to fix the base sections of the main wire to respective teeth of the patient. For this, the base section may, in particular, comprise substantially straight sections of the main wire. In an even more preferred embodiment, in an unconstrained state of the main wire, the base section extends parallel to the first and second end sections. This allows the use of brackets commonly used for fastening to a patient's teeth.

In some embodiments, in the unconstrained state, the main wire may define a principal line of extension with the first and second end sections and a base section extending parallel to the principal line of extension.

In a preferred embodiment, the main wire has at least two coupling means, each being arranged on a respective one of the looped sections.

In these embodiments, the support wire may be coupled to the main wire at at least two different locations. This results in a more favorable force distribution. Moreover, the arrangement of the main wire in the patient's mouth may be controlled in more detail. The at least two coupling means may, in particular, be arranged at an apex of a respective one of the looped sections.

In an even more preferred embodiment, the main wire has first and second coupling means, the first coupling means being arranged on a first looped section of the series and a second coupling means being arranged on a last looped section of the series.

In these embodiments, the two coupling means are arranged at a large distance from each other. This results in an even more favorable stress distribution along the main wire.

In a preferred embodiment, the fastening means comprise first and second fasteners adapted to be fastened to a respective tooth and having attachment means for the first or second end section of the main wire, respectively.

The fasteners provide a convenient way to attach the main wire and/or the support wire to the patient's teeth. In particular, the fasteners may be fastened to the teeth before applying the main wire or the support wire. Here, it is even more preferred that the first and second fastener have attachment means for a first and second end section of the support wire, respectively. In these embodiment, only two fasteners are needed to attach, both, the main wire and the support wire to the patient's teeth.

According to a preferred embodiment, the coupling means comprises a wound structure.

This provides an easy way to form the coupling means from the main wire. In some embodiment, the wound structure may further comprise a semi-circle of wire. In other embodiments, the wound structure may comprise one or more full circles of wire. The wound structure may be formed from the main wire or may be formed from a separate wire.

In a preferred embodiment, the support wire comprises tightening means for adjusting a length and/or a tension thereof.

In these embodiments, applying the system to a patient's denture is facilitated. In particular, the orthodontic system may be put into its final position by tightening the support wire by means of the tightening means.

In an even more preferred embodiment, the tightening means comprises a knob.

The knob facilitates the handling of the device when applying it to the patient's tooth. In particular, the knob may be turned in order to tighten the support wire. In some embodiments, the knob may be formed from the support wire. In other embodiments, the knob may comprise a separate component being attached to the support wire.

According to a preferred embodiment, in the unconstrained state of the main wire, the at least one looped section extends substantially transversely, in particular perpendicularly to the first and second end sections.

In these embodiments, the leverage effect of the looped section is increased. Moreover, the looped sections have a well defined extension with respect to the first and second end sections of the main wire. It is even more preferred that in embodiments with more than one looped section, the looped sections extend substantially parallel to each other in the unconstrained state of the main wire. In these embodiment, the looped sections are arranged in a well defined manner when the orthodontic system supplied to the patient's teeth. In particular, in the applied state the looped sections are directed towards the roots of the patients teeth.

According to a preferred embodiment, the main wire further comprises at least one attachment means for attaching the main wire to a respective bracket fastened to a tooth, wherein, preferably the attachment means comprises a wound structure.

The attachment means facilitates the attachment of the main wire to the patient's teeth by means of a bracket being fastened to a This is especially advantageous if the attachment means is arranged at a position of the main wire which corresponds to a position of strong curvature of the patient's teeth. Moreover, a wound structure is especially advantageous as it is easy to form on the main wire and may easily be attached to a standard bracket. In some embodiments, the attachment means comprises a wound structure being formed on the main wire, while in other embodiments, the attachment means may comprise a wound structure being formed from a separate wire.

In an even more preferred embodiment, the at least one attachment means comprises two attachment means arranged at the first and second end section of the main wire.

In these embodiments, the attachment means are arranged towards the first and second end sections of the main wire. This leads to a better force distribution along the main wire.

Moreover, in embodiments with five looped sections, the attachment means may be arranged to lie in front of the patient's left and right canines. As the human denture shows a natural curvature in this area, this arrangement is preferred as it helps to arrange the main wire around the natural curvature.

According to a preferred embodiment, the main wire and/or the support wire comprises stainless steel. Generally, it is preferred that the main wire and the support wire comprise materials that do not corrode and that resist the environment in a patient's mouth. Moreover, for the main wire, a certain level of flexibility is useful when applying the main wire to the patient's denture.

In particular it is preferred that the main wire is manufactured from spring hard stainless steel wire. The wire size of the main wire may further be between 0.2 mm and 0.6 mm, in particular between 0.3 mm and 0.5 mm and most preferably between 0.35 mm and 0.45 mm. Alternatively or additionally, the support wire may comprise dead soft stainless steel wire. The wire size of the support wire may further be between 0.1 mm and 0.4 mm, in particular between 0.15 mm and 0.35 mm and preferably between 0.2 mm and 0.3 mm. These wire sizes provide a compromise between the required robustness and flexibility, cost and material usage.

In some embodiments, the looped sections may define a clearance along the principal extension of the main wire of between 1 mm and 5 mm, in particular, between 2 mm and 4 mm and preferably between 2.5 mm and 3.5 mm. Alternatively or additionally, the looped sections may have a length of between 5 mm and 20 mm, in particular between 8 mm and 15 mm and preferably between 9 mm and 13 mm. Alternatively or additionally, the coupling means may comprise a wound structure with a diameter of between 1 mm and 5 mm, in particular between 2 mm and 4 mm and preferably between 2.5 mm and 3.5 mm. Alternatively or additionally, the attachment means may comprise a wound structure with a diameter of between 1 mm and 5 mm, in particular between 2 mm and 4 mm and preferably between 2.5 mm and 3.5 mm. Alternatively or additionally, the attachment means may be spaced at a clearance from an adjacent looped section of between 1 mm and 5 mm, in particular between 1.5 mm and 3 mm. Alternatively or additionally, the base section may have a length of between 5 mm and 15 mm, in particular between 6 mm and 12 mm and preferably between 7 mm and 10 mm. Alternatively or additionally, the first and second end sections may have a length of between 10 mm and 70 mm, in particular between 20 mm and 60 mm and preferably between 30 mm and 55 mm.

In a preferred embodiment, the orthodontic system is further arranged to provide an anteriorly directed force to the teeth of between 50 grams and 200 grams (between 0.49 N and 1.96 N) and, in particular between 100 grams and 150 grams (between 0.98 N and 1.47 N).

In a further aspect, the present invention provides an orthodontic system of the aforementioned type for use in the treatment of retruded maxilla, in particular, in the treatment of class III malocclusion with retruded maxilla, cleft lip and palate with retruded maxilla, or a craniofacial abnormality with retruded maxilla.

In a still further aspect, the present invention provides or can be used for a method for applying the orthodontic device of the aforementioned kind to the teeth of a patient, the method comprising the following steps:

(F) Fastening the first and second end sections of the main wire to a first and second tooth, respectively, using the fastening means, (A) coupling the support wire to the at least one coupling means of the main wire and attaching a first and a second end section of the support wire to respective teeth using the fastening means and tightening the support wire.

In a preferred method, the step of (F) fastening the first and second end sections of the main wire further comprises
(F1) fastening the first and second fasteners to a first and a second tooth, respectively, and
(F2) attaching the first and second end sections of the main wire to the first and second fastener, respectively.

In a preferred method, attaching a first and second end section of the support wire to respective teeth further comprises attaching the first and second end sections of the support wire to the first and second fastener, respectively.

According to a preferred method, tightening the support wire comprises actuating the tightening means of a support wire.

In a preferred method, the method further comprises the step of (L) litigating the main wire to at least one bracket being fastened to a respective tooth. Here, it is even more preferred that the step (1) is carried between steps (F) and (A).

It is even more preferred that the step of (L) litigating the main wire to at least one bracket being fastened to a respective tooth further comprises litigating the first or second end section or a base section of the main wire to the at least one bracket.

Further features and advantages of the present invention can be seen from the following description of a preferred embodiment of the present invention.

Figure 1:
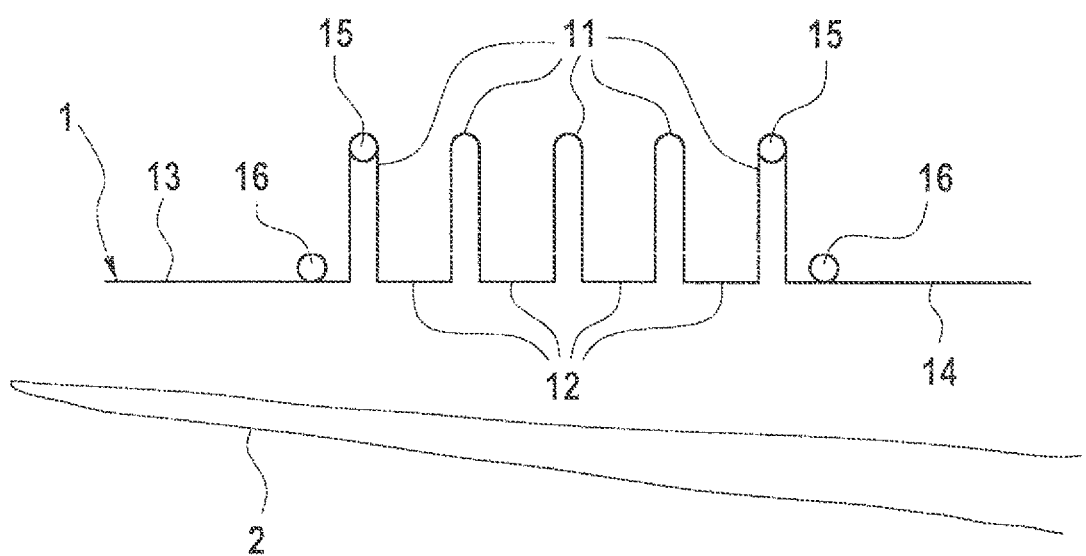
FIG. 1 shows a main wire and a support wire of the system according to an embodiment of the present invention, the main wire being in an unconstrained state.

In the preferred embodiment shown in FIG. 1, the orthodontic system of the present invention comprises a main wire 1 and a support wire 2. FIG. 1 shows the main wire 1 in an unconstrained state. The main wire 1 comprises a first end section 13 and a second end section 14 at opposite ends thereof. Moreover, the main wire 1 comprises first and second attachment means 16 being arranged at the first and second end sections 13, 14, respectively. In the embodiment of FIG. 1, the first and second attachment means 16 take the form of wound structures. These are dimensioned to be arranged at the patient's canines. In particular, the first and second attachment means 16 comprise the main wire 1 being wound into a respective wound structure. In other embodiments, the attachments means may comprise the main wire being wound in multiple windings and/or may imply a separate wound structure like, e.g. a ring, being attached to the main wire.

In the embodiment of FIG. 1, the main wire 1 further comprises five looped sections. The looped sections 11 are arranged as a series along the main wire 1. Each two adjacent looped sections 11 are interconnected by a respective base section 12. In the unconstrained state shown in FIG. 1, the first and second end sections 13, 14 and the four base sections 12 are substantially parallel to each other and define a principal line of extension of the main wire 1. In particular, the first and second end sections 13, 14 and the base sections 12 form a straight line in the unconstrained state of the main wire 1 shown in FIG. 1.

A first and last looped section 15 of the series of looped sections of the main wire 1 is further provided with a respective coupling means 15 for coupling the main wire 1 to the support wire 2. In the embodiment of FIG. 1, the coupling means 15 take the form of a wound structure. Here, the main wire 1 is wound into a respective wound structure in order to form a coupling means 15. In other embodiments, the coupling means may comprise the main wire being wound in multiple windings and/or may imply a separate wound structure like, e.g. a ring, being attached to the main wire.

In the embodiment of FIG. 1, each of the base sections 12 comprises a substantially straight section of the main wire 1. Moreover, the first and second end sections 13, 14 each comprise a respective substantially straight section of the main wire 1. Each of the looped sections 11, moreover, comprises two substantially parallel straight lengths of wire.

The main wire 1 according to the shown embodiment may comprise the following dimensions: The looped sections 11 may have a width of about 3 mm and a length of about 11 mm. Further, the coupling means 15 and attachment means 16 may each comprise a winding with a diameter of 3 mm. Further, the attachment means 16 may be spaced at a 2 mm clearance from an adjacent looped section 11. The first and the last of the looped sections 11 in the series may be spaced from the second and the next to last looped section, respectively, at a clearance of 7 mm, while the three central looped sections have a clearance of 10 mm between adjacent looped sections 11. The first and second end sections 13, 14 may further extend for 50 mm before or after the attachment means 16, respectively.

Figure 2:
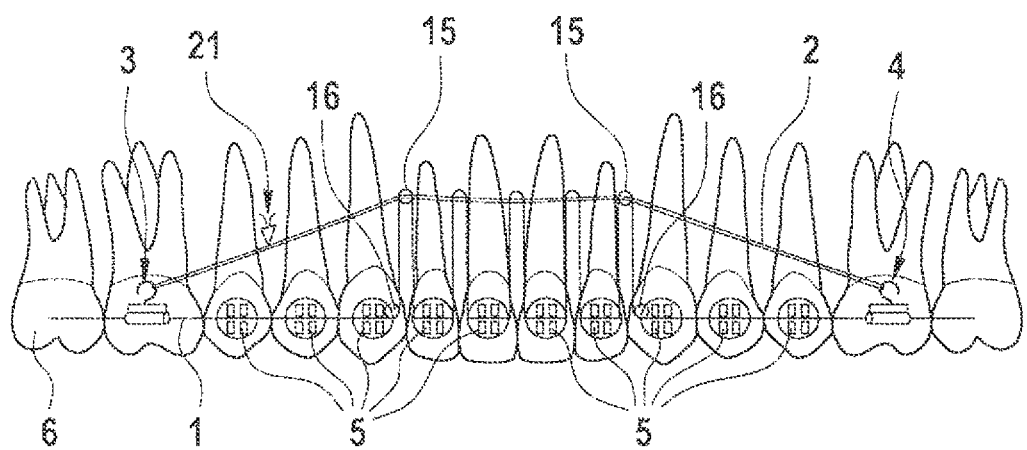
FIG. 2 shows a schematic frontal view of the orthodontic system according to the embodiment of the present invention in the applied state.

FIG. 2 shows the embodiment of the orthodontic system of the present invention in the applied state with the main wire 1 being in a constrained state. As FIG. 2 is a schematic drawing, the curvature of the patient's teeth is not shown. In the orthodontic system of FIG. 2, the support wire 2 has been tied into a knot which acts as a tightening means 21.

The orthodontic system of FIG. 2, moreover, comprises a first 3 and a second 4 fastener. In this embodiment, the first and second fasteners 3, 4 are molar tubes. The fasteners 3, 4 are arranged to be attached to the first and second end sections 13, 14 of the main wire 1 by means of tubes being arranged on the fasteners. Moreover, the fasteners 3, 4 are provided with a respective hook to attach to first and second ends of the support wire 2, respectively. The hook comprises an open position and a closed position. In the open position, a looped end of the support wire 2 may be mounted onto the hook. For this purpose, in the open position, a gap is formed between an end of the hook and a corresponding part of the fastener 3, 4. The hook may be moved from the open position to the closed position by means of an instrument. In the closed position, the support wire is prevented from slipping from the hook.

The looped sections 11 are arranged as to be located at the transition between adjacent teeth in the applied state of the orthodontic system.

Also shown in FIG. 2 is a number of brackets 5 being fastened to respective teeth 6. The main wire 1 is litigated to the brackets 5. In more detail, the first and second end sections 13, 14 and the base sections 12 are litigated to the brackets 5. Moreover, the attachment means 16 which in this embodiment take the form of canine loops are litigated to canine brackets.

In the embodiment of FIG. 2, the orthodontic system is applied to the upper anterior teeth of the patient. In other embodiments, the orthodontic system may be arranged to be applied to the lower anterior teeth. Further, in some embodiments, the orthodontic system is adapted to be applied to only 1, 2 or 3 anterior teeth.

In the applied state shown in FIG. 2, the support wire 2 extends from the first fastener 3 to a first coupling means 15 to a second coupling means 15 and from there to the second fastener 4. Between the first fastener 3 and the first coupling means 15, the support wire 2 comprises the tightening means 21.

In the applied state of the orthodontic system shown in FIG. 2, the main wire 1 and the support wire 2 are in a constrained state. In particular, the tightening means 17 is applied to generate a tension force along the support wire 2.

Figure 3A:
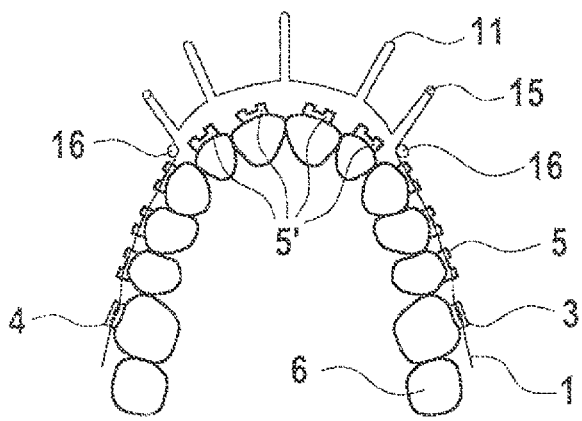
FIG. 3a shows a schematic bottom view of the patient's upper teeth along with the orthodontic system according to the embodiment of the present invention at a stage of applying the orthodontic system in front of the patient's teeth.
Figure 4A:
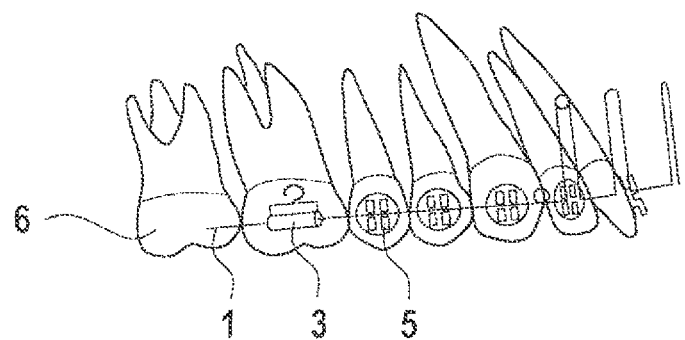
FIG. 4a shows a side view of the patient's upper teeth along with the orthodontic system of the embodiment of the present invention at a stage of applying the orthodontic system to the patient's teeth.

FIGS. 3a, b, c and FIGS. 4a, b, c show the orthodontic system in various stages of applying the system to the patient's teeth. In FIG. 3a the first and second end sections 13, 14 of the main wire 1 are attached to the first and second fastener 3, 4 respectively. In the arrangement of FIG. 3a, the looped sections 11 extend anteriorly in front of the patient's teeth.

Figure 3B:
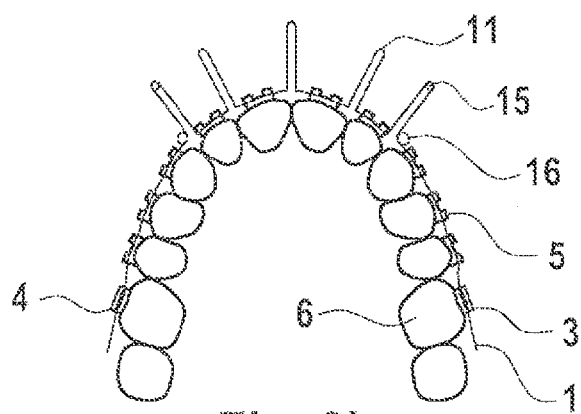
FIG. 3b shows a schematic bottom view of the patient's upper teeth along with the orthodontic system according to the embodiment of the present invention at a stage of fastening the orthodontic system to the patient's teeth.
Figure 3C:
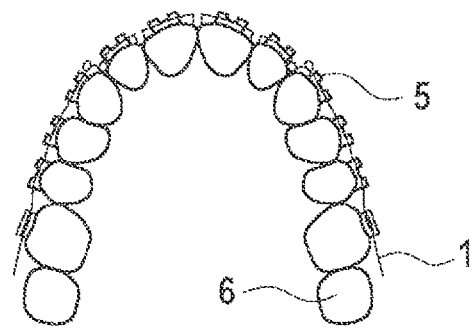
FIG. 3c shows a schematic bottom view of the patient's upper teeth along with the orthodontic system according to the embodiment of the present invention at a stage fastened in front of the patient's teeth.
Figure 4B:
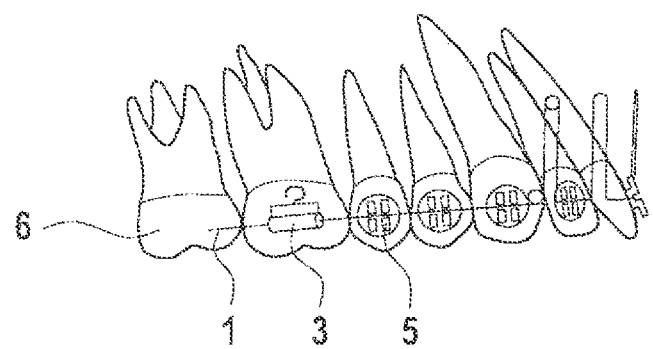
FIG. 4b shows a side view of the patient's upper teeth along with the orthodontic system of the embodiment of the present invention at a stage of fastening the orthodontic system to the patient's teeth.
Figure 4C:
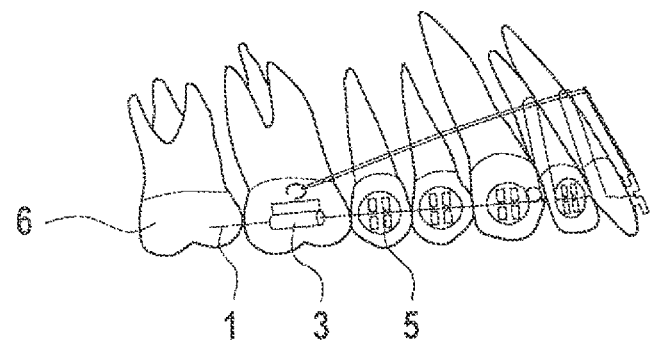
FIG. 4c shows a side view of the patient's upper teeth along with the orthodontic system of the embodiment of the present invention at a stage fastened to the patient's teeth.

In a next step, the attachment means 16 in the form of canine loops are litigated to respective canine brackets fastened to the patient's canines. Then, as shown in FIGS. 3b and 4b, the first and second end sections and the base sections 12 of the main wire 1 are litigated to respective brackets 5, 5' being fastened to the patient's teeth.

In a next step, the support wire 2 is attached to one of the fasteners and is further coupled to the main wire 1 by means of the coupling means 15 and is then attached to the other fastener. The support wire 2 is then tightened by actuating the tightening means 21 (not shown in FIGS. 3a, b, c and 4a, b, c). This way, the looped sections 12 of the main wire are refracted to the vestibular sulcus and towards to roots of the teeth.

Figure 5:
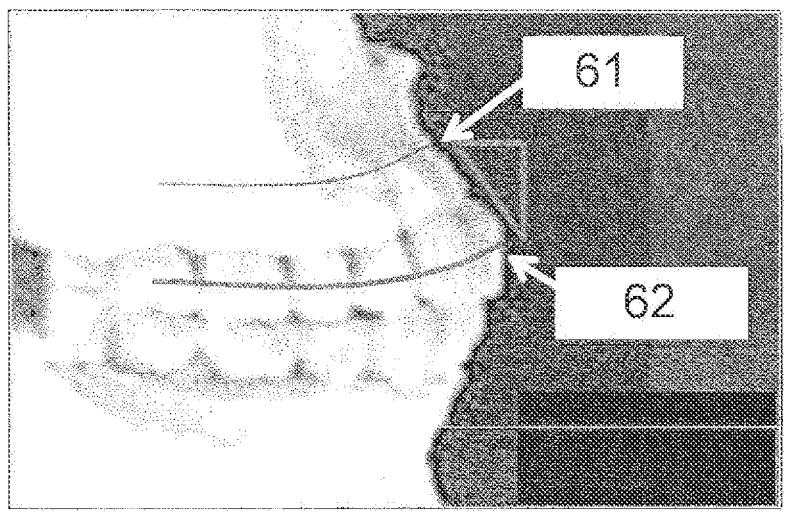
FIG. 5 shows an x-ray image of a patient's denture in side view.

FIG. 5 shows an x-ray image of a patient's denture. Here, it can be seen that the line of circumference at the crowns 62 of the teeth is larger than the line of circumference at the position of the roots 61. In the applied state of the orthodontic system, the base sections 12 are positioned along the crowns 62, while the looped sections 11 are drawn towards the roots. Hence, a distal force is generated along the main wire 1, which is transferred to the teeth by means of the brackets 5'. This leads to protracting forces urging the crowns 62 in a generally anterior direction.

REFERENCE NUMERALS 1 main wire
11 looped section
12 base section
13 first end section
14 second end section
15 coupling means
16 attachment means
2 support wire
21 tightening means
3 first fastener
4 second fastener
5, 5' bracket
6 tooth
61 roots
62 crowns

The invention claimed is:

1. An orthodontic system comprising:
a main wire having first and second end sections and at least two looped sections arranged as a series between the first and second end sections, and
a support wire disposed on either an upper jaw or a lower jaw,
the main wire being ligated to a number of brackets to be fastened to respective teeth,
the support wire comprising means for adjusting a length and/or a tension thereof to tighten the support wire,
the main wire further having at least two means for coupling to the support wire, each of the means for coupling being arranged on an apex of a respective one of the looped sections and comprising a wound structure comprising at least one full circle of wire, and
means for fastening the main wire and the support wire to a patient's teeth, wherein the means for fastening comprises first and second fasteners adapted to be fastened to a respective tooth and having means for attaching the first or second end section of the main wire, respectively, the first and second fasteners being molar tubes, wherein the first and second fasteners further have means for attachment to a first or second end section of the support wire, respectively, and wherein the support wire is coupled to the means for coupling by the support wire passing through the at least one full circle of wire.

2. The system of claim 1, wherein each two adjacent looped sections are interconnected by a respective base section, wherein in an unconstrained state of the main wire the base section extends parallel to the first and second end sections.

3. The system of claim 2, wherein the main wire further comprises at least one means for attachment for attaching the main wire to a respective bracket fastened to a tooth and at least one of the at least one means for attachment of the main wire is arranged at a respective base section thereof.

4. The system of claim 1, the main wire having first and second coupling means, the first coupling means being arranged on a first looped section of the series and the second coupling means being arranged on a last looped section of the series.

5. The system of claim 1, wherein the tightening means comprises a knob.

6. The system of claim 1, wherein in an unconstrained state of the main wire, the at least one looped section-extends substantially transversely, to the first and second end sections.

7. The system of claim 6, wherein the at least one looped section-extends in particular perpendicularly to the first and second end sections.

8. The system of claim 1, wherein the main wire further comprises at least one means for attachment for attaching the main wire to a respective bracket fastened to a tooth.

9. The system of claim 8, wherein the at least one attachment means comprises two means for attachment arranged at the first or second end section of the main wire.

10. A method for treatment of retruded maxilla, comprising applying the orthodontic system of claim 1 to the upper or lower anterior teeth of a patient.

11. The method of claim 10 wherein the treatment of retruded maxilla comprises the treatment of class III malocclusion with retruded maxilla, cleft lip and palate with retruded maxilla, or a craniofacial abnormality with retruded maxilla.

* * * * *